United States Patent [19]

Kirmann

[11] Patent Number: Plant 6,021

[45] Date of Patent: Sep. 22, 1987

[54] GERANIUM PLANT NAMED SALLY

[75] Inventor: Wolfgang Kirmann, Langenzersdorf, Austria

[73] Assignee: Mirko Vavra, Bisamberg, Austria

[21] Appl. No.: 811,154

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Sally having bright red-purple flower color with a small, dark red-purple variegation on upper two petals; compact, floriferous, self-branching growth habit; early flowering; good bud production at night temperatures up to 16° C., thus providing a long and continuous flowering period; medium green foliage; and ease of propagation and good rooting habit.

2 Drawing Figures

The present invention comprises a new and distinct cultivar of geranium, botanically known as *Pelargonium domesticum,* and hereinafter referred to by the cultivar name Sally.

Sally is a product of a planned breeding program which had the objective of creating new geranium cultivars having a very floriferous, compact growth habit, red-purple flower color, very early flowering, and large petals.

Sally was originated from a hybridization made by applicant in a controlled breeding program in Bisamberg, Austria in 1980. The female parent was a cultivar designated as seedling lilac/2, having a very vigorous growth habit, early flowering and long flowering period, and large petals. The male parent of Sally was Venedig, characterized by its tall growth habit, excellent flower production and dark red-purple color.

Sally was discovered and selected as one flowering plant within the progeny of the stated cross by applicant on Mar. 15, 1981 in a controlled environment in Bisamberg, Austria.

The first act of asexual reproduction of Sally was accomplished when vegetative cuttings were taken from the initial selection on Aug. 30, 1981 in a controlled environment in Bisamberg, Austria by a technician working under formulations established and supervised by Wolfgang Kirmann. Horticultural examination of selected units initiated in the spring of 1982 has demonstrated that the combination of characteristics as herein disclosed for Sally are firmly fixed and are retained through successive generations of asexual reproduction.

Sally has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Sally, which in combination distinguish this geranium as a new and distinct cultivar.

1. Bright red-purple flower color, variegated with dark red-purple at approximate center of upper petals.
2. Propagates well, with very good rooting habit.

3. Excellent bud production and very floriferous.
4. Compact, self-branching growth habit.
5. Early flowering and long flowering period.
6. Medium green foliage.
7. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
8. Sally is unique with regard to the combined features of compactness, continuous flowering, floriferous habit, and red-purple flower color.

Of the many commercial cultivars known to the present inventor, the most similar in comparison to Sally is Jubilante, an unpatented but commercial cultivar. In comparison to Jubilante, Sally has a more compact growth habit, flowers earlier with better flower production, and has a more uniform red-purple flower color.

The accompanying photographic drawings show typical flower and foliage characteristics of Sally, with colors being as true as possible with illustrations of this type.

Sheet 1 is a perspective view of a potted plant of Sally.

Sheet 2 is a black and white print showing the upper surface of immature and mature plants of Sally.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Sally.

INFLORESCENCE

A. Umbel:

*Average diameter.*—Medium; 95-120 mm.

*Peduncle length.*—Normal.

*Pedicel length.*—Normal.

B. Corolla:

*Average diameter.*—65–80 mm; total inflorescence diameter is within the foliage.

*Form.*—Five petals.

*Color (general tonality from a distance of three meters).*—Bright red-purple with small dark red-purple variegation near throat on upper petals.

*Color (upper surface).*—68B, variegated near throat with 59A.

C. Bud:

*Shape.*—Elongated.

*Color.*—Lilac.

D. Reproductive organs:

*Androecium.*—Yellow; 7 stamens.

*Gynoecium.*—Five to six part lobed stigma.

E. Spring flowering response period: Early.

F. Durability: Very good.

PLANT

A. Foliage:

*Form.*—Zygomorphic with a nectar spur.

*Margin.*—Crenate with spaced indentations.

*Color (upper surface).*—Medium green.

*Tolerance of Botrytis and soil fungi.*—Excellent.

B. General appearance and form:

*Internode length.*—Short.

*Branching pattern.*—Excellent.

*Height.*—Compact.

I claim:

1. A new and distinct cultivar of geranium named Sally, as described and illustrated, and particularly characterized by its bright red-purple flower color with small, dark red-purple variegation on upper two petals; compact, floriferous, self-branching growth habit; early flowering; good bud production at night temperatures up to 16° C., thus providing a long and continuous flowering period; medium green foliage; and by its ease of propagation and good rooting habit.

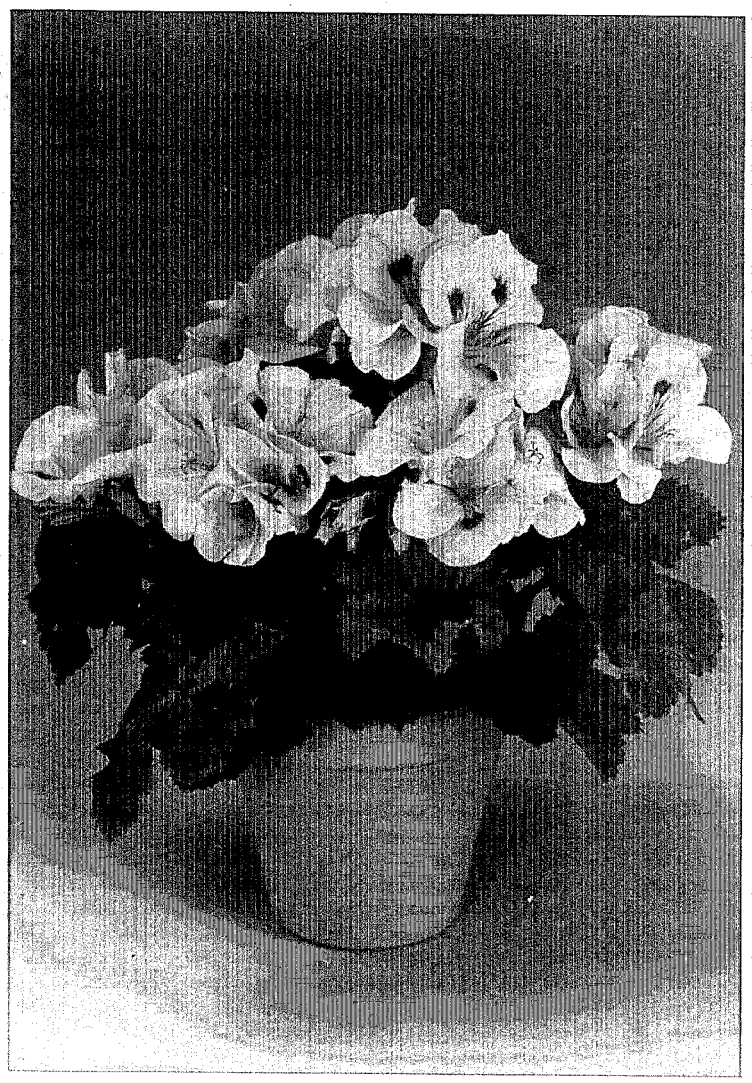

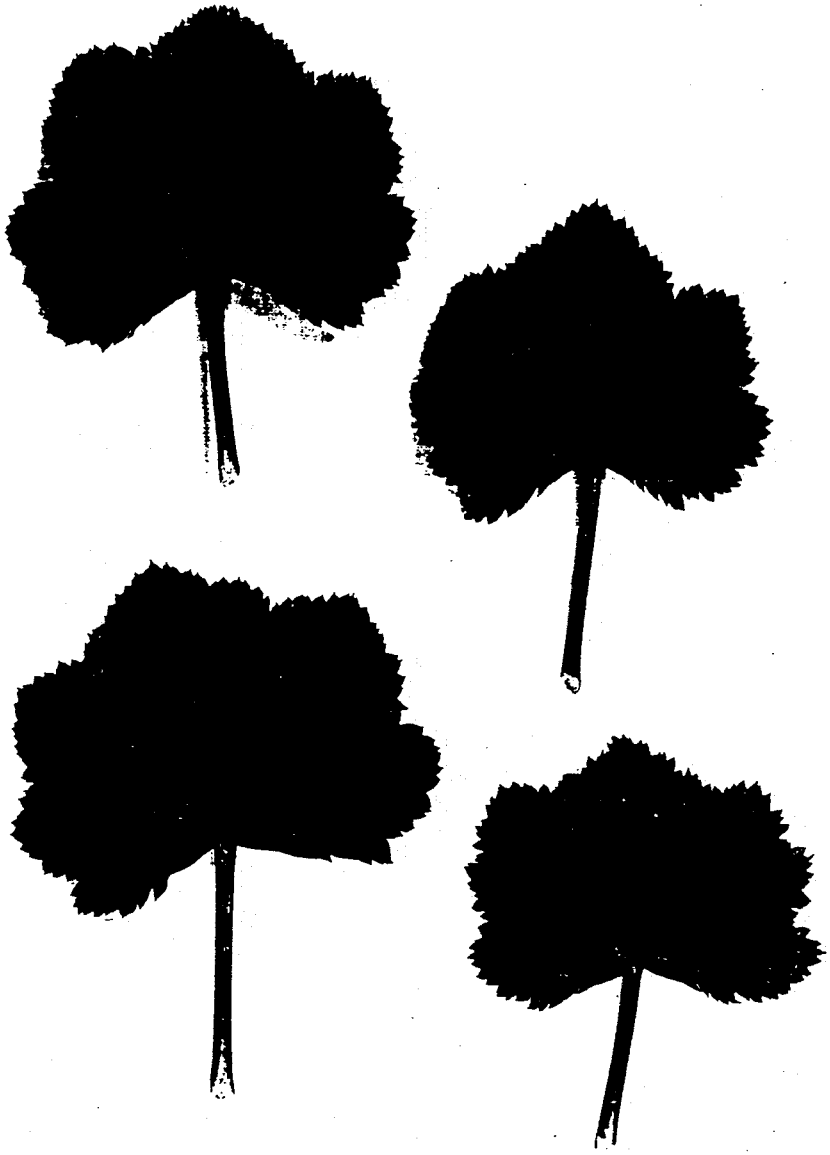

* * * * *